(12) United States Patent
Yeh et al.

(10) Patent No.: US 9,352,127 B2
(45) Date of Patent: May 31, 2016

(54) CLOSED-SYSTEM CATHETER ASSEMBLY

(71) Applicant: CareFusion 303, Inc., San Diego, CA (US)

(72) Inventors: Jonathan Yeh, Diamond Bar, CA (US); George Mansour, Pomona, CA (US); Chris Zollinger, Chino Hills, CA (US)

(73) Assignee: CareFusion 303, Inc., San Diego, CA (US)

( * ) Notice: Subject to any disclaimer, the term of this patent is extended or adjusted under 35 U.S.C. 154(b) by 467 days.

(21) Appl. No.: 13/673,975

(22) Filed: Nov. 9, 2012

(65) Prior Publication Data
US 2014/0135703 A1    May 15, 2014

(51) Int. Cl.
*A61M 5/178*   (2006.01)
*A61M 25/06*   (2006.01)

(52) U.S. Cl.
CPC ....... *A61M 25/0606* (2013.01); *A61M 25/0631* (2013.01); *A61M 25/0693* (2013.01)

(58) Field of Classification Search
CPC ..................... A61M 25/0606; A61M 25/0631; A61M 25/0693
USPC ........................................ 604/164.09–164.12
See application file for complete search history.

(56) References Cited

U.S. PATENT DOCUMENTS

| | | | |
|---|---|---|---|
| 5,885,251 A * | 3/1999 | Luther | 604/161 |
| 6,547,762 B1 * | 4/2003 | Botich et al. | 604/110 |
| 2010/0204648 A1 * | 8/2010 | Stout et al. | 604/122 |

FOREIGN PATENT DOCUMENTS

| | | |
|---|---|---|
| EP | 812602 A2 | 12/1997 |
| WO | WO-2012/009459 A1 | 1/2012 |
| WO | WO-2012/106266 A1 | 8/2012 |

OTHER PUBLICATIONS

International Search Report and Written Opinion from International Application No. PCT/US2013/068151, dated May 12, 2014.
International Preliminary Report on Patentability for International Application No. PCT/US2013/068151, dated Nov. 24, 2014, 5 pages.

* cited by examiner

*Primary Examiner* — Rebecca E Eisenberg
(74) *Attorney, Agent, or Firm* — McDermott Will & Emery LLP

(57) ABSTRACT

A catheter system including an insertion device and a catheter device. The insertion device includes a housing, a latch, a needle for insertion into a patient; and a spring. The catheter device includes a housing comprising a chamber, and a seal disposed in said chamber. The seal is configured to reseal when the needle is withdrawn from the seal such that blood is sealed in the chamber. The spring relaxes and thereby retracts the needle entirely into the housing of the insertion device when the latch decouples from the catheter device.

19 Claims, 7 Drawing Sheets

CLOSED-SYSTEM CATHETER ASSEMBLY

BACKGROUND OF THE INVENTION

Typically, it may be difficult to couple a catheter to extension devices while also preventing blood leakage.

FIELD OF THE INVENTION

The invention generally relates to the field of catheters and catheter systems incorporating extension devices that attach to the catheter.

DESCRIPTION OF THE RELATED ART

Traditional catheter and extension systems require the catheter device to be coupled to the extension system via threads, which necessitates a rotating motion to couple and uncouple the devices. There exists a need for an easier and more efficient way to couple and uncouple these systems.

BRIEF SUMMARY OF THE INVENTION

In a first embodiment, a catheter insertion device comprises a housing, a latch for resiliently coupling the housing to a catheter device, a needle for insertion into a patient and a spring, wherein said spring relaxes and thereby retracts the needle entirely into the housing when the latch resiliently decouples from the catheter device.

In a second embodiment, a catheter device comprises a housing comprising a chamber and a seal disposed in the chamber, wherein the seal is configured to reseal when a needle of the catheter insertion device is withdrawn from the seal such that blood is sealed in the chamber.

In a third embodiment, a catheter system comprises an insertion device that comprises a housing, a latch, a needle for insertion into a patient and a spring; and a catheter device coupled to the insertion device, the catheter device comprising a housing comprising a chamber and a seal disposed in the chamber, wherein the seal is configured to reseal when the needle is withdrawn from the seal such that blood is sealed in the chamber, and wherein the spring relaxes and thereby retracts the needle entirely into the housing of the insertion device when the latch decouples from the catheter device.

In a fourth embodiment a catheter device comprises a housing comprising a coupling feature for coupling the catheter device to another device, wherein the coupling feature does not require threads.

The drawings referred to in this description should be understood as not being drawn to scale except if specifically noted.

DETAILED DESCRIPTION OF THE INVENTION

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, and components have not been described in detail as not to unnecessarily obscure aspects of the present embodiments.

Figure 1:
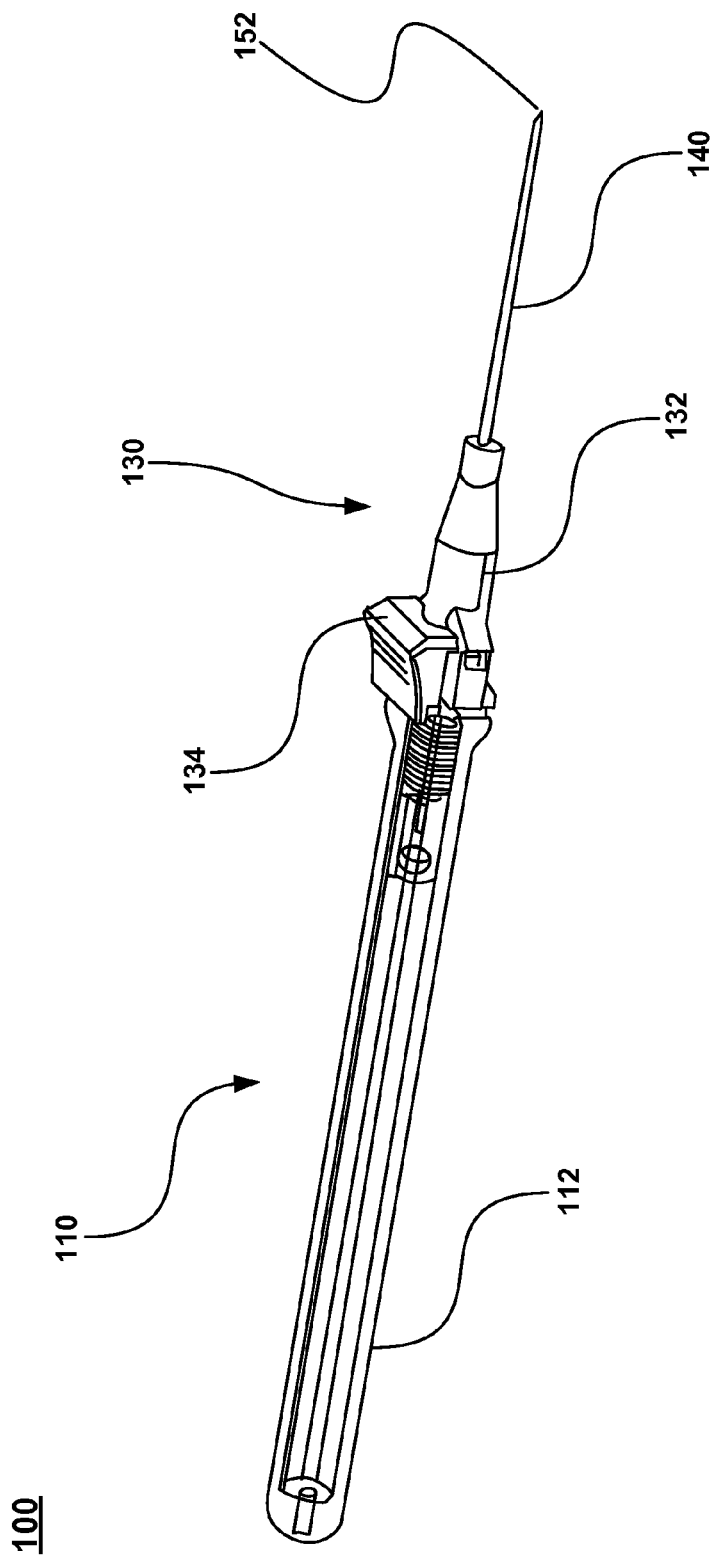
FIG. 1 is a perspective view of an embodiment of the catheter system in a pre-insertion state.
Figure 2:
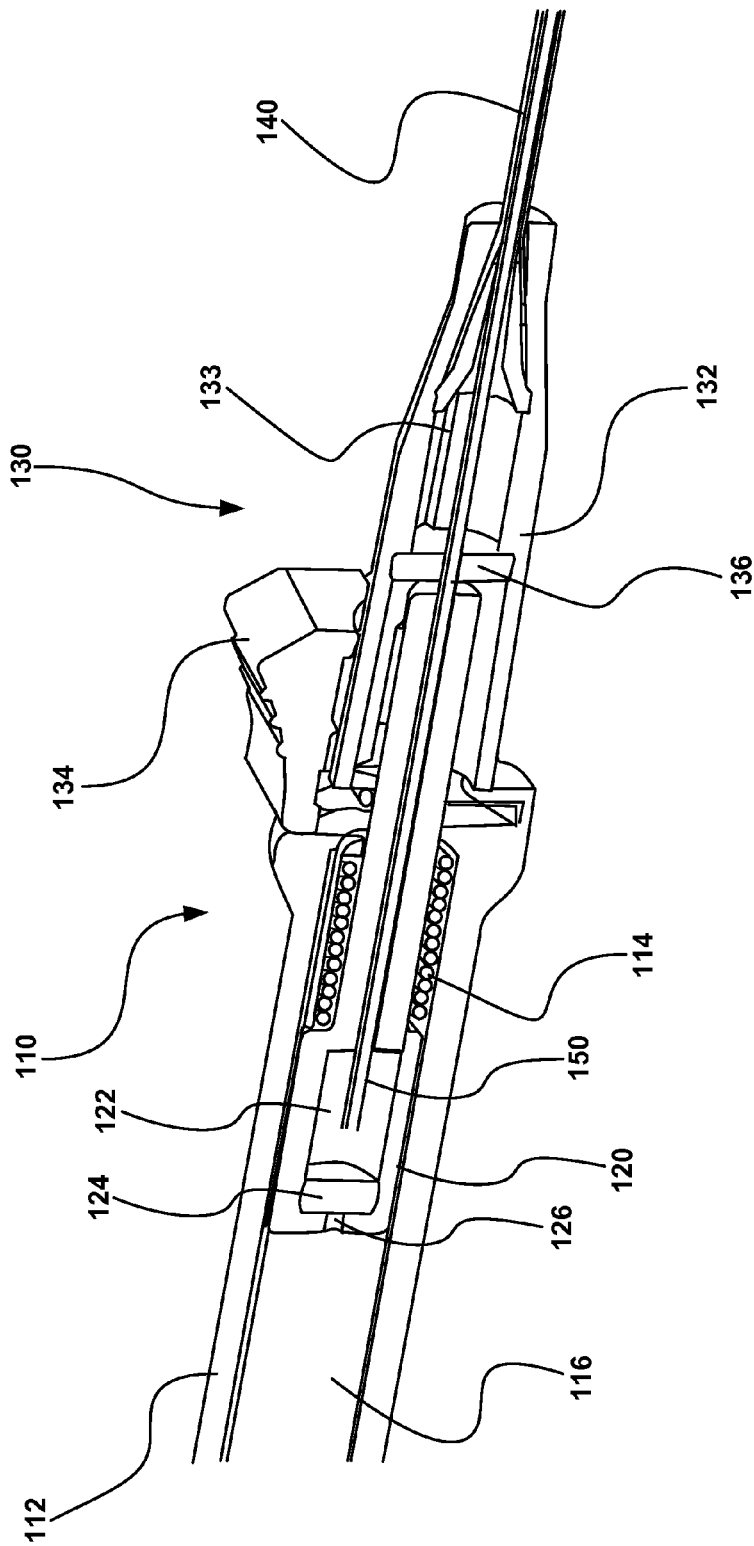
FIG. 2 is a cross-sectional view of the catheter system of FIG. 1 in a pre-insertion state.

FIG. 1 depicts an embodiment of catheter system 100 (or catheter assembly) in a pre-insertion state. FIG. 2 depicts a cross-sectional view of the catheter system 100 in the pre-insertion state. A pre-insertion state is the state of catheter system 100 prior to inserting the catheter into a patient.

Catheter system 100 includes catheter insertion device 110 coupled to catheter device 130. Catheter insertion device 110 is resiliently coupled to catheter device 130 via latch 134. In one embodiment, latch 134 is a spring latch that flexibly and resiliently engages (e.g., snap fit) with any physical features (e.g., protrusions, indentions, etc.) on housing 132 of catheter device 130. It should be appreciated that catheter insertion device 110 is coupled to catheter device 130 without requiring a threaded coupling.

In contrast, conventional catheter systems a catheter device is coupled to an insertion device via threads. As such, the insertion device must be rotated to couple/decouple it from the catheter device.

In one embodiment, latch 134 resiliently couples to internal features of catheter device 130. In another embodiment, latch 134 is rotatable with respect to catheter device 130 when resiliently coupled to catheter device 130.

Needle 150 is held by needle collet 120. An end of needle 150 is disposed in viewing chamber 122. When in the pre-insertion state, the tip 152 of the needle 150 extends through and out of catheter device 130 and is also disposed within catheter 140.

Moreover, in the pre-insertion state, spring 114 is compressed and abuts against needle collet 120.

During insertion, needle 150 and catheter 140 are inserted into a vein of a patient. When properly inserted, blood travels within needle 150 to viewing chamber 122. In particular, the blood does not come into contact with any internal surface of (e.g., chamber 133) of catheter device 130 when catheter insertion device 110 is coupled to catheter device 130.

When blood is provided in viewing chamber 122, the blood is able to be viewed through housing 112 and needle collet 120 to provide a visual indication that needle 150 and catheter 140 have been properly inserted into the vein. As such, both housing 112 and needle collet 120 are either translucent or transparent.

The blood is sealed in viewing chamber by filter 124. In one embodiment, filter 124 is a hydrophobic filter. In particular, when blood enters into viewing chamber 122, air passes through filter 124 and exits vent 126 into ambient. However, the blood is not able to pass through filter 124.

In order to withdraw needle 150 from the vein, catheter insertion device 110 is withdrawn from catheter device 130. However, latch 134 still remains in contact with and is coupled to catheter device 130 via features on housing 132. During withdrawal, needle 150 is also withdrawn through catheter 140 (which remains in the vein).

Figure 3:
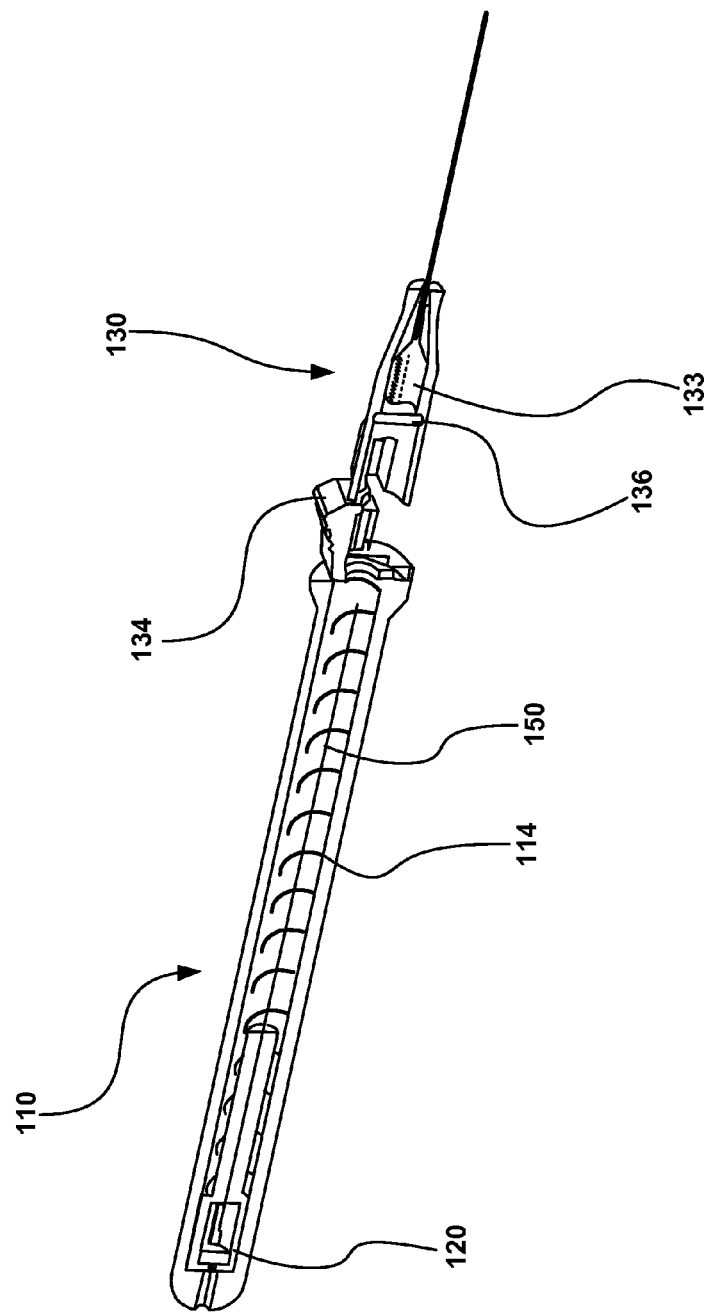
FIG. 3 is a cross sectional view of the catheter system showing the needle completely withdrawn from the catheter.

Once latch 134 is completely decoupled from catheter device 130 (e.g., latch 134 does not engage with retaining features on housing 132), spring 114 is released into its relaxed state. In doing so, spring 114 urges needle collet 120 such that it axially slides within chamber 116. As a result, needle 150 is completely withdrawn through catheter device 130 and is entirely disposed within housing 112, as depicted in FIG. 3. In other words, needle 150 is automatically withdrawn from the vein and through catheter device 130 when latch 134 is decoupled from housing 132. When no longer coupled to catheter device 130, catheter insertion device 110 may be properly discarded.

Once needle 150 is withdrawn through seal 136, seal 136 reseals. As such, blood entering into chamber 133, via catheter 140 is sealed within chamber 133 to prevent blood loss. Therefore, catheter device 130 is also a closed system because blood is securely sealed within chamber 133. In one embodiment, seal 136 is a silicone disc. In another embodiment, seal 136 is pre-slit to facilitate in the insertion/withdrawal of device (e.g., needle 150).

Figure 4:
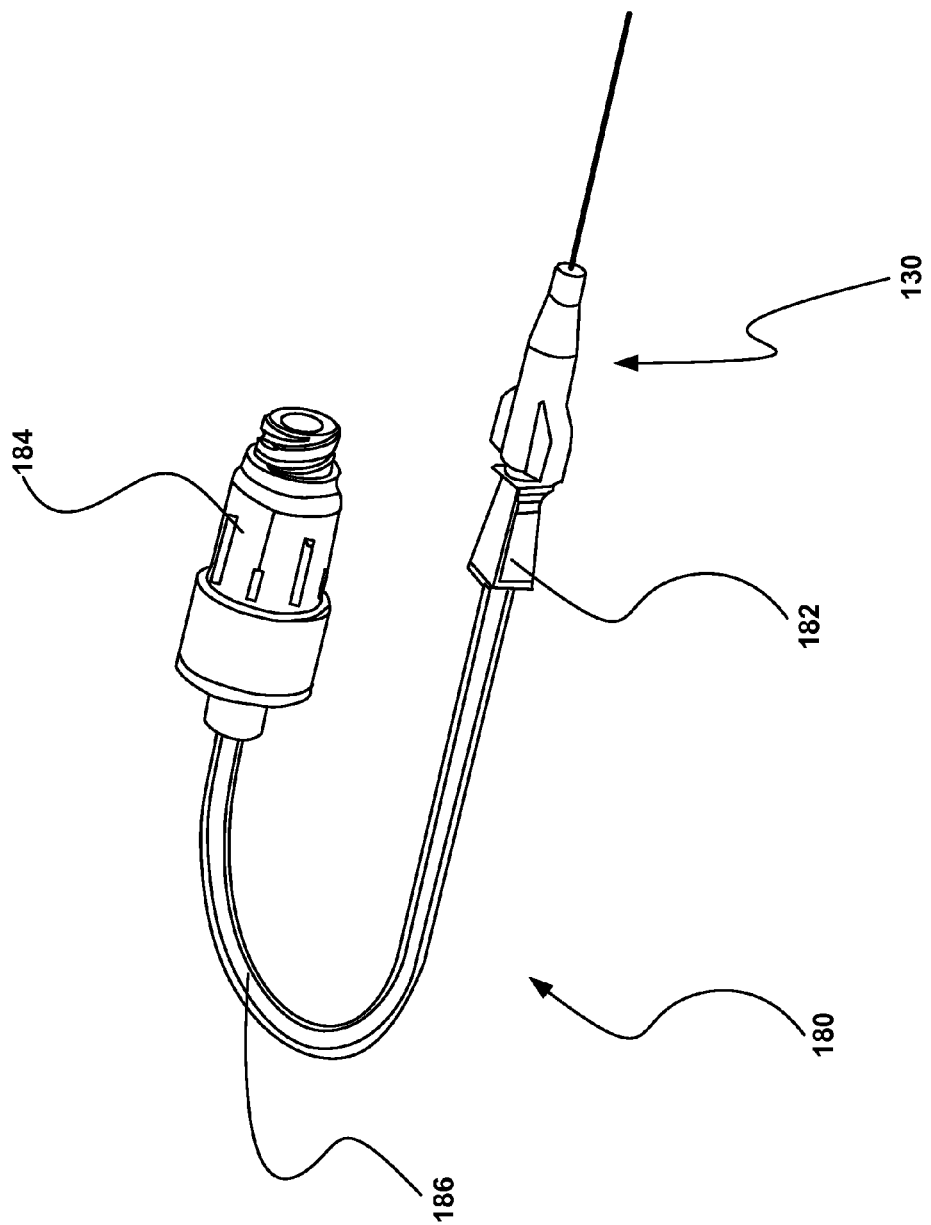
FIG. 4 is a perspective view of an embodiment of an extension set coupled to a catheter device.
Figure 5:
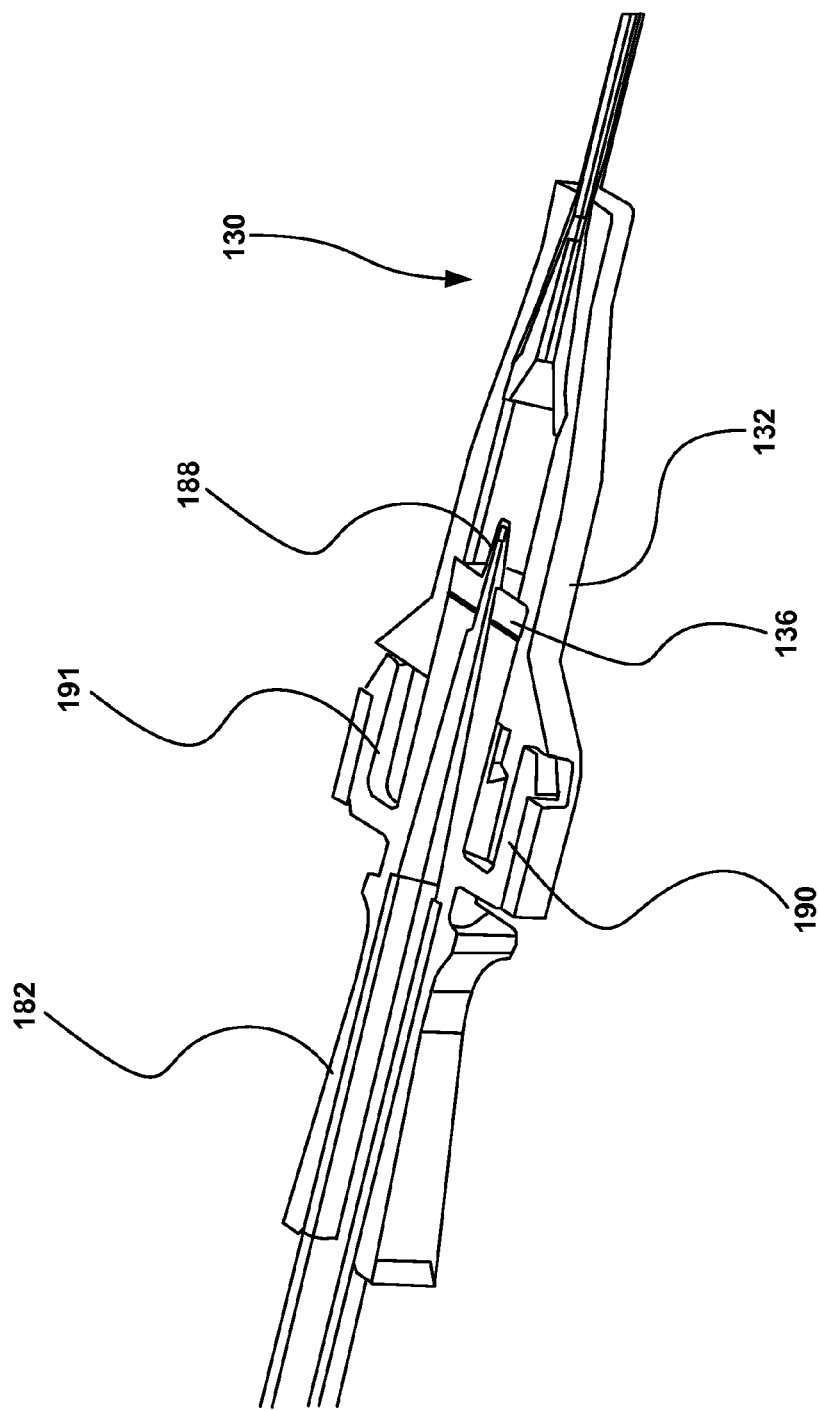
FIG. 5 is a cross-sectional view of the extension set of FIG. 4 coupled to a catheter device.

FIG. 4 depicts an embodiment of extension set 180 coupled to catheter device 130. FIG. 5 depicts a cross-sectional view of extension set 180 coupled to catheter device 130.

In order to couple extension set 180 to catheter device 130, a user grasps base 182 an inserts cannula 188 through seal 136 until coupling features 190 and 191 (e.g., tines) mechanically couple (e.g., snap fit) with associated coupling features of housing 132. The coupling may be provided by use of a single hand of a user.

In contrast, in conventional systems, the extension set is rotatably coupled to the catheter via threads. Moreover, a user must use both hands to couple the catheter to the extension set. For example, a user must hold onto the catheter and use the other hand to handle the extension set and rotated with respect to the catheter.

When properly coupled, blood is able to flow through tube 186 to luer access device 184. It should be appreciated that any compatible disposable set or extension set may be coupled to catheter device 130.

Figure 6A:
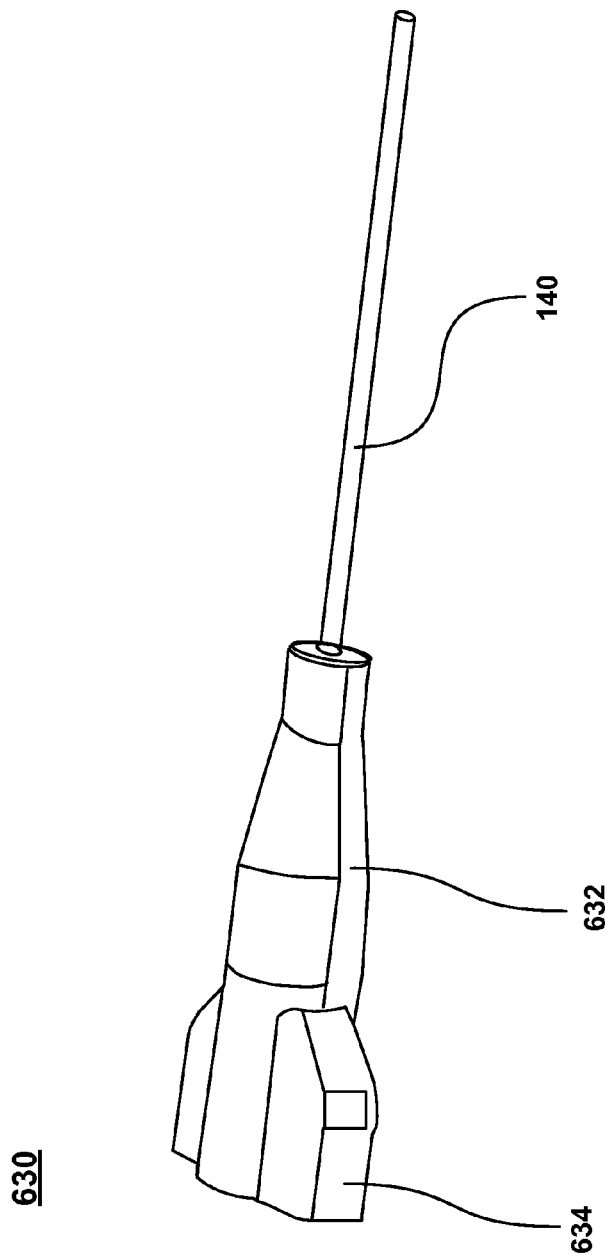
FIG. 6A is a perspective view of another embodiment of the catheter device.
Figure 6B:
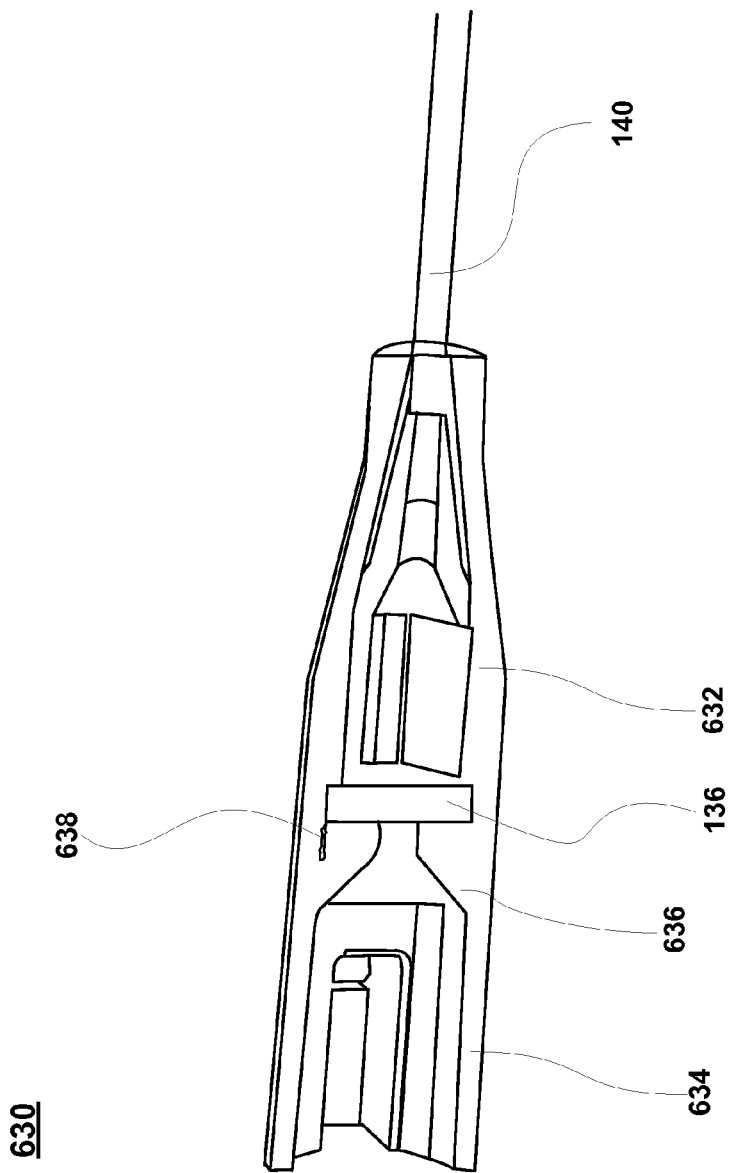
FIG. 6B is a cross-sectional view of the embodiment of FIG. 6A.

FIGS. 6A-B depict an embodiment of catheter device 630. Catheter device 630 includes first section 632 that is joined to second section 634. The joining can be but is not limited to an ultrasonic weld, adhesive, snap fit, etc. Seal 136 is placed between first section 632 and second section 634 prior to joining and is securely seated between first section 632 and second section 634 when the sections are joined at joint 638.

In one embodiment, second section 634 includes funnel 636 to facilitate in the guiding of needle 150 through catheter device 630 during assembly such that needle 150 is properly aligned to puncture seal 136.

It should be appreciated that embodiments, as described herein, can be utilized or implemented alone or in combination with one another. While the present invention has been described in particular embodiments, it should be appreciated that the present invention should not be construed as limited by such embodiments, but rather construed according to the following claims.

The invention claimed is:

1. A catheter insertion device comprising:
   a housing;
   a latch, coupled to and extending from said housing, said latch comprising an external portion configured to snap-fit with at least one corresponding feature on a catheter device housing of a catheter device for resiliently coupling said housing to said catheter device;
   a needle for insertion into a patient, said needle coupled to a needle collet that is slidably disposed within said housing; and
   a spring coupled to said needle collet, wherein said latch comprises a first position in which an internal portion of said latch prevents extension of said spring and a second position in which said internal portion releases said spring to extend such that said spring relaxes and thereby retracts said needle entirely into said housing, and wherein said latch is configured to be held in said first position by said catheter device housing and to be released to said second position when said latch resiliently decouples from said catheter device.

2. The catheter insertion device of claim 1, further comprising:
   a viewing chamber, wherein blood in said viewing chamber is able to be viewed through said housing.

3. The catheter insertion device of claim 2, further comprising:
   a hydrophobic filter disposed in said viewing chamber, wherein said hydrophobic filter allows air to vent and seals said blood in said viewing chamber.

4. The catheter insertion device of claim 1, wherein said needle collet is axially slidably disposed in said housing, and wherein, when said latch is released to said second position, said spring urges said needle collet to slide within said housing away from said latch.

5. The catheter insertion device of claim 1, wherein blood passes through said catheter device via said needle into a viewing chamber disposed in a needle collet.

6. The catheter insertion device of claim 1, wherein said at least one corresponding feature on said catheter device housing comprises one or more external features of said catheter device.

7. The catheter insertions device of claim 1, wherein said catheter insertion device is a closed system.

8. A catheter device comprising:
   a housing comprising a chamber;
   a seal disposed in said chamber, wherein said seal is configured to reseal when a needle of a catheter insertion device is withdrawn from said seal such that blood is sealed in said chamber; and
   wherein said housing comprises at least one external feature configured to snap fit with a latch that extends from a catheter insertion device housing of said catheter insertion device to maintain said needle in a position in which said needle passes through said seal in a configuration in which said housing is resiliently coupled with said catheter insertion device by said latch.

9. The catheter of claim 8, wherein said catheter device is a closed system.

10. The catheter of claim 8, wherein said housing further comprises internal features configured to receive coupling features of an extension set to snap fit said housing with said extension set.

11. The catheter of claim 10, wherein said seal comprises:
    a silicone seal.

12. The catheter of claim 11, wherein said seal is configured to be punctured by a cannula of said extension set such that said blood is able to exit said chamber into said extension set.

13. The catheter of claim 8 wherein said housing comprises:
a funnel proximate said seal.

14. The catheter of claim 8, wherein said seal is disposed proximate a joint between a first section and a second section.

15. A catheter system comprising:
an insertion device comprising:
a housing;
a latch, coupled to and extending from said housing, said latch comprising an external portion;
a needle for insertion into a patient, said needle coupled to a needle collet that is slidably disposed within said housing; and
a spring coupled to said needle collet; and
a catheter device,
said catheter device comprising:
a housing comprising a chamber and at least one feature configured to snap fit with said external portion of said latch of said insertion device; and
a seal disposed in said chamber, wherein said seal is configured to reseal when said needle is withdrawn from said seal such that blood is sealed in said chamber,
wherein said latch comprises a first position in which an internal portion of said latch prevents extension of said spring and a second position in which said internal portion releases said spring to extend such that said spring relaxes and thereby retracts said needle entirely into said housing of said insertion device, and wherein said latch is configured to be held in said first position by said housing of said catheter device and to be released to said second position when said latch decouples from said catheter device.

16. The catheter system of claim 15, wherein said spring is compressed when said catheter device is coupled to said insertion device and said latch is in said first position.

17. The catheter system of claim 15, wherein said insertion device is configured such that blood passes through said catheter via said needle into a viewing chamber disposed in said needle collet.

18. The catheter system of claim 15, wherein said seal is configured to be punctured by an extension set such that said blood is able to exit said chamber into said extension set.

19. The catheter system of claim 15,
wherein said needle collet is axially slidably disposed in said housing of said insertion device, and wherein, when said latch is released to said second position, said spring urges said needle collet to slide within said housing away from said late.

* * * * *